(12) United States Patent
Francis et al.

(10) Patent No.: US 7,870,007 B1
(45) Date of Patent: Jan. 11, 2011

(54) SYSTEM AND METHOD OF DETERMINING INTERACTIONS BETWEEN MEDICINES

(75) Inventors: John Brian Francis, Alpharetta, GA (US); John C. Goodwin, III, Suwanee, GA (US)

(73) Assignee: NCR Corporation, Duluth, GA (US)

( * ) Notice: Subject to any disclaimer, the term of this patent is extended or adjusted under 35 U.S.C. 154(b) by 1968 days.

(21) Appl. No.: 10/191,236

(22) Filed: Jul. 9, 2002

(51) Int. Cl.
*G06Q 10/00* (2006.01)
*G06F 19/00* (2006.01)

(52) U.S. Cl. .............................. 705/2; 705/3
(58) Field of Classification Search ................. 705/2–3
See application file for complete search history.

(56) References Cited

U.S. PATENT DOCUMENTS

| | | | |
|---|---|---|---|
| 5,845,255 A * | 12/1998 | Mayaud | 705/3 |
| 5,845,264 A * | 12/1998 | Nellhaus | 705/28 |
| 6,068,156 A * | 5/2000 | Liff et al. | 221/7 |
| 6,188,570 B1* | 2/2001 | Borkowski | 361/683 |
| 6,283,761 B1* | 9/2001 | Joao | 434/236 |
| 6,493,427 B1* | 12/2002 | Kobylevsky et al. | 379/67.1 |
| 6,625,581 B1* | 9/2003 | Perkowski | 705/27 |

OTHER PUBLICATIONS

Anonymous. "Interactive Pharmacy Kiosks" Jun. 1990. Chain Store Age Executive with Shopping Center Age. vol. 66, Iss. 6. p. 49.*
Anonymous. "Thrift Drug Keeps in Touch: In-Store Kiosks Provide Customer Assistance" Jun. 1987. Chain Store Age Executive with Shopping Center Age. vol. 63, Iss. 6. p. 58.*
Anonymous. "Self Help" Feb. 1999. Progressive Grocer. vol. 78, Iss. 2. p. 14.*

* cited by examiner

*Primary Examiner*—Robert W Morgan

(57) ABSTRACT

A system and method of determining interactions between medicines which includes a pharmacy kiosk. One embodiment of the pharmacy kiosk includes a display, an input device, and a computer for displaying a prompt to enter medicine identification information for a medicine, for recording the medicine identification information, for obtaining interaction information between the medicine and other medicines, and for displaying the interaction information. The computer may additionally record operator identification information, obtain prescriptions of the operator for the other medicines using the operator identification information, obtain interaction information between the medicine and the other medicines, and display the interaction information.

18 Claims, 4 Drawing Sheets

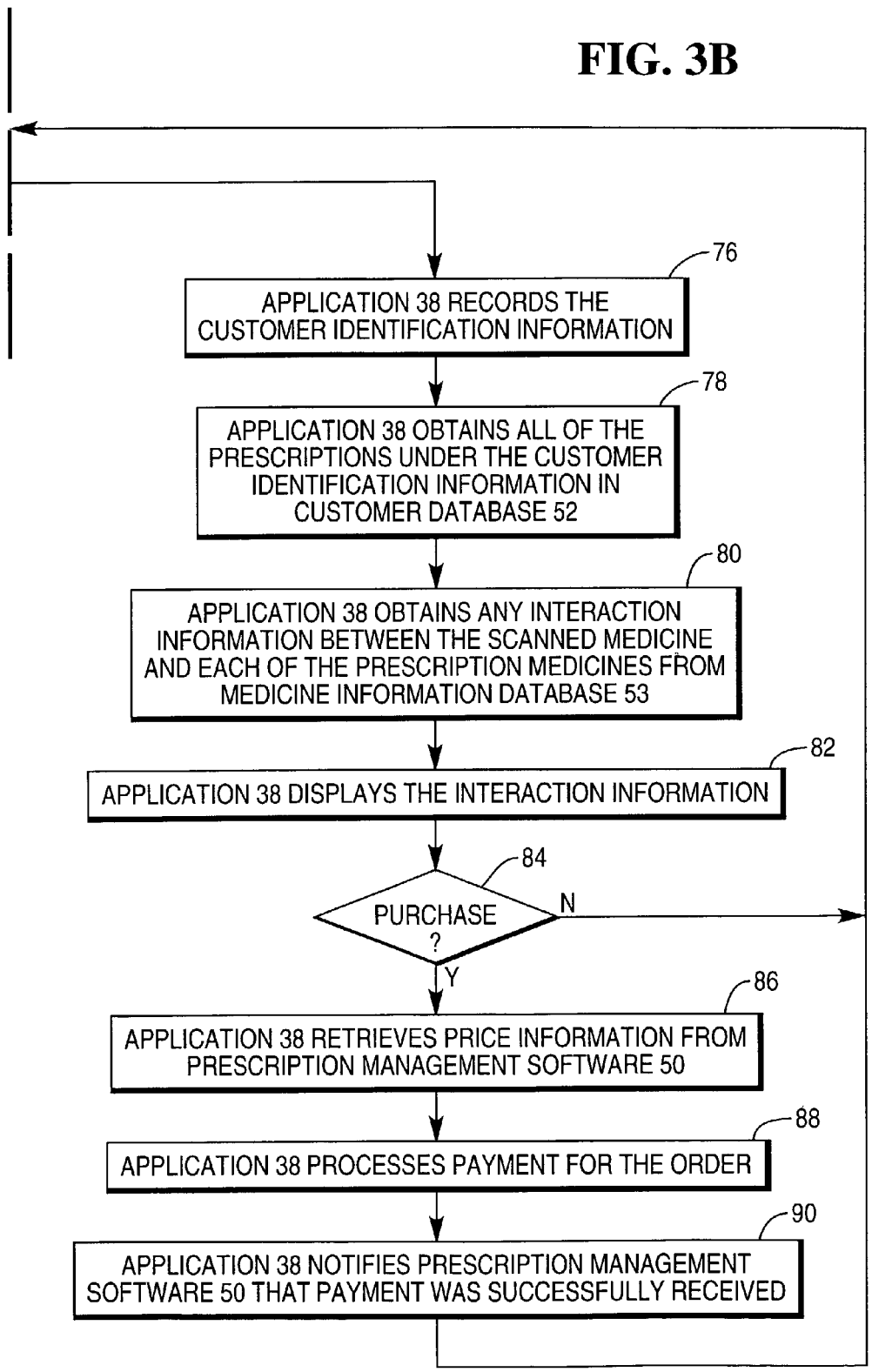

SYSTEM AND METHOD OF DETERMINING INTERACTIONS BETWEEN MEDICINES

CROSS-REFERENCE TO RELATED APPLICATIONS

The present invention is related to the following commonly assigned co-pending U.S. applications filed therewith:

Application Ser. No. 10/191,125, entitled "SYSTEM AND METHOD OF COMPLETING A PHARMACY TRANSACTION", having as inventor, John Goodwin;

Application Ser. No. 10/191,234, entitled "SYSTEM AND METHOD OF REFILLING A PRESCRIPTION", having as inventor, John Goodwin;

Application Ser. No. 10/190,666, entitled "SYSTEM AND METHOD OF REFILLING A PRESCRIPTION", having as inventor, John Goodwin.

BACKGROUND OF THE INVENTION

The present invention relates to self-service kiosks and more specifically to a system and method of determining interactions between medicines.

Self-service terminals include kiosks. Kiosks provide a publicly accessible computing platform for displaying World Wide Web (web) pages and other web-delivered content from web sites. Kiosks may be located within a retailer's transaction establishment or elsewhere, such as in shopping malls. Kiosks may be easily networked to web sites using the TCP/IP protocol. Web pages from web sites may be displayed using known and available web software, such as Microsoft® Internet Explorer software.

Major retailers who have pharmacies seek an effective way to complete pharmacy transactions. Pharmacy customers must pay for prescription medicines at store checkout lanes. For customers who only seek to obtain prescription medicine or other pharmacy items, waiting in line at checkout lanes adds extra time to their visits in the store.

Therefore, it would be desirable to provide a pharmacy kiosk which would allow the pharmacy customer to pay for prescription medicines using a pharmacy kiosk. It would also be desirable for the customer to be able to determine whether there are any interactions between medicine the customer wishes to purchase and other medicines, including the medicine the customer is already taking.

SUMMARY OF THE INVENTION

In accordance with the teachings of the present invention, a system and method of determining interactions between medicines is provided.

One embodiment of the pharmacy kiosk includes a display, an input device, and a computer for displaying a prompt to enter medicine identification information for a medicine, for recording the medicine identification information, for obtaining interaction information between the medicine and other medicines, and for displaying the interaction information.

In another embodiment the computer records operator identification information, obtains prescriptions of the operator for the other medicines using the operator identification information, obtains interactions information between the medicine and the other medicines, and displays the interaction information.

The method of determining interaction information between a medicine and other medicines includes the steps of displaying a prompt to enter medicine identification information for the medicine by a pharmacy kiosk, recording the medicine identification information for the medicine by the pharmacy kiosk, obtaining the interaction information by the pharmacy kiosk, and displaying the interaction information by the pharmacy kiosk.

Another embodiment of the method includes the steps of displaying a prompt to enter operator identification information by the pharmacy kiosk, recording the operator identification information by the pharmacy kiosk, obtaining prescriptions of the operator for the other medicines using the operator identification information by the pharmacy kiosk, obtaining interaction information between the medicine and the other medicines by the pharmacy kiosk, and displaying the interaction information by the pharmacy kiosk.

It is accordingly an object of the present invention to provide a system and method of determining interactions between medicines.

It is another object of the present invention to enable payment for prescription medicines at a pharmacy kiosk.

It is another object of the present invention to provide a method of identifying any interactions between medicine a customer wishes to purchase and other medicine, including medicine the customer is already taking.

BRIEF DESCRIPTION OF THE DRAWINGS

Additional benefits and advantages of the present invention will become apparent to those skilled in the art to which this invention relates from the subsequent description of the preferred embodiments and the appended claims, taken in conjunction with the accompanying drawings, in which:

FIGS. 3A and 3B form a flow diagram illustrating the method of the present invention.

DETAILED DESCRIPTION OF THE PREFERRED EMBODIMENT

Figure 1:
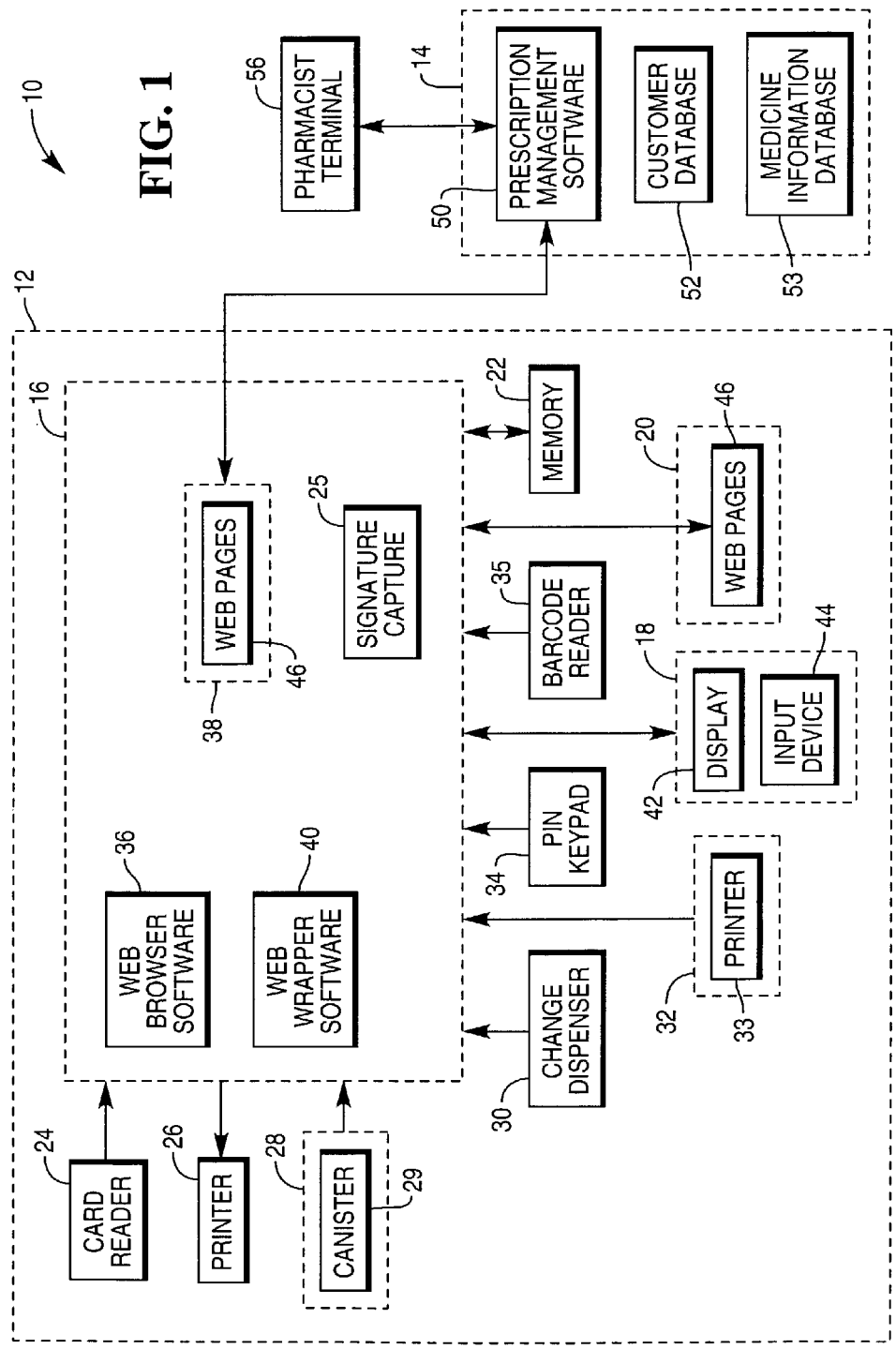
FIG. 1 is a block diagram of a first embodiment of a pharmacy system.
Figure 2:
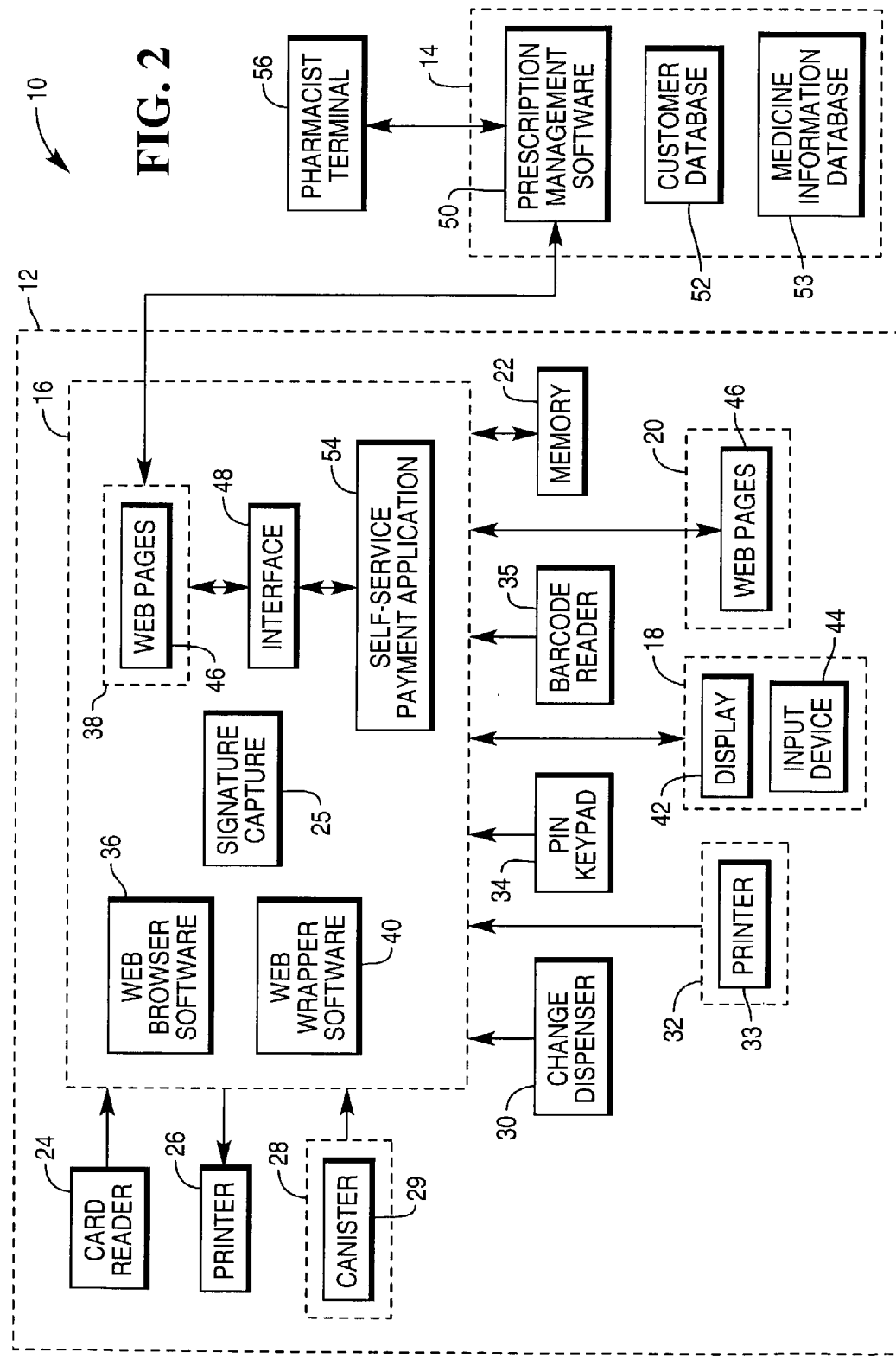
FIG. 2 is a block diagram of a second embodiment of the pharmacy system.

Turning now to FIGS. 1 and 2, system 10 includes kiosk 12 and pharmacy management system 14. Kiosk 12 is preferably located in a retail establishment. Kiosk 12 may include an NCR 7401 computer.

Kiosk 12 is a self-service terminal which primarily includes processor 16, touch screen 18, memory 22, and disk storage 20. Kiosk 12 may optionally include a number of peripherals to enhance operation for ordering and paying for prescription medicine and other pharmacy products. The peripherals may include cash acceptor 28, cash dispenser 30, check reader 32, and personal identification number (PIN) keypad 34.

Kiosk 12 additionally includes barcode reader 35 for scanning barcode labels on medicine containers, receipts, paper, labels, and other media. The barcode labels contain medicine identification information. Touch screen 18 may also be used to enter medicine identification information.

Processor 16 executes application 38, which guides a customer through a pharmacy transaction. Application 38 records pharmacy customer identification information, retrieves prescription information and cost from pharmacy management system 14, and displays instructions for completing ordering of medications.

In a first embodiment (FIG. 1), application 38 records payment via card reader 24, cash acceptor 28, or check reader 32, and dispenses change through cash dispenser 30. Following receipt of payment, application 38 sends a message to pharmacy management system 14 indicating that the transaction was successful.

In a second embodiment (FIG. 2), application 38 offloads payment processing to self-service payment application 54. Application 38 passes cost details to self-service payment application 54 via interface 48. Following receipt of payment, self-service payment application 54 notifies application 38, which in turn notifies pharmacy management system 14. This embodiment saves development costs for stores by allowing them to use the same application for self-service kiosks and self-service checkout lanes.

In either embodiment, application 38 may record customer signatures and store them electronically for later analysis.

Application 38 may include OPOS (Object Linking and Embedding for Point of Sale) software. OPOS is a technology that enables hardware independence for POS solution providers on Win32 platforms. The industry standard defines a method of interfacing to POS peripherals.

Application 38 communicates with pharmacy management system 14 over a network connection, such as one which uses the TCP/IP protocol. Kiosk 12 may be connected to the World Wide Web (web) and may obtain web content from web servers. Pharmacy management system 14 may be an external web server.

Processor 16 may also execute web browser software 36 and web wrapper software 40.

Web browser software 36 allows an operator to display information in a format established by the World Wide Web (WWW or "web"). Application 38 may be written as a web application which displays pharmacy transaction information in the form of web pages 46, although application 38 may also be a non-web application and operate without web browser software 36 and web wrapper software 40. Web pages 46 may be written using hypertext markup language (HTML) or other suitable web page language.

Web browser software 36 may include commercially available web browser software, such as Microsoft® Internet Explorer web browser software. Microsoft® Internet Explorer web browser software is configured into a kiosk operation using a "-k" command line option. This option hides toolbars and menu bars to prevent operator access to those functions.

Web browser software 36 may also display a start or "home" page within web pages 46 which operates as a default page from which kiosk operation begins and to which operation returns when an operator is finished using kiosk 12. Web browser software 36 may also facilitate purchase of goods from retailers and may also serve to display advertisement when not in use.

Web wrapper software 40 provides security functions. During operation, web wrapper software 40 prevents an operator from accessing kiosk files, or other applications, or the operating system software, or basic input-output system (BIOS) firmware, and prevents the operator from causing kiosk 12 to reboot.

Touch screen 18 includes display 42 and input device 44. Display 42 and input device 44 may also be separate units. Input device 44 may record order selection information from a pharmacy customer.

Disk storage 20 is a first storage medium used by processor 16 which stores web pages 46 for use by application 38 and other applications. Some of web pages 46 may be obtained from web servers.

Memory 22 is a second storage medium used by processor 16 to store executed program information.

Card reader 24 reads loyalty, credit, debit, SMART, and/or other types of cards carried by a pharmacy customer. Card reader 24 may record payment information from a pharmacy customer.

In either embodiment, application 38 may record customer signatures and store them electronically for later analysis.

Signature capture unit 25 captures customer signatures.

Printer 26 prints receipt information.

Cash acceptor 28 includes currency storage canister 29. Cash acceptor 28 takes in currency, validates the currency, sends tendered amount information to application 38, and sends currency count information to application 38. Cash acceptor 28 may include a cash acceptor manufactured by CashCode or Mars.

Cash dispenser 30 dispenses change.

Check reader 32 reads checks and includes a magnetic ink character (MICR) reader. Check reader 32 also includes printer 33 for printing information on checks.

PIN keypad 34 records PIN numbers for debit card transactions.

Pharmacy management system 14 executes pharmacy management software 50, which sends price information to kiosk 12 and updates customer accounts following successful payment. Pharmacy management software 50 stores customer identification and order information in customer database 52.

Pharmacy management software 50 also has access to medicine interaction information in medicine information database 53.

Pharmacist terminal 56 allows a pharmacist to access customer database 52 to determine orders that need filling and whether payment has been made before filling an order. If payment has not been made, then the pharmacist will know to attach a bill or provide other indication that payment must be made before the customer leaves the store.

Figure 3A:
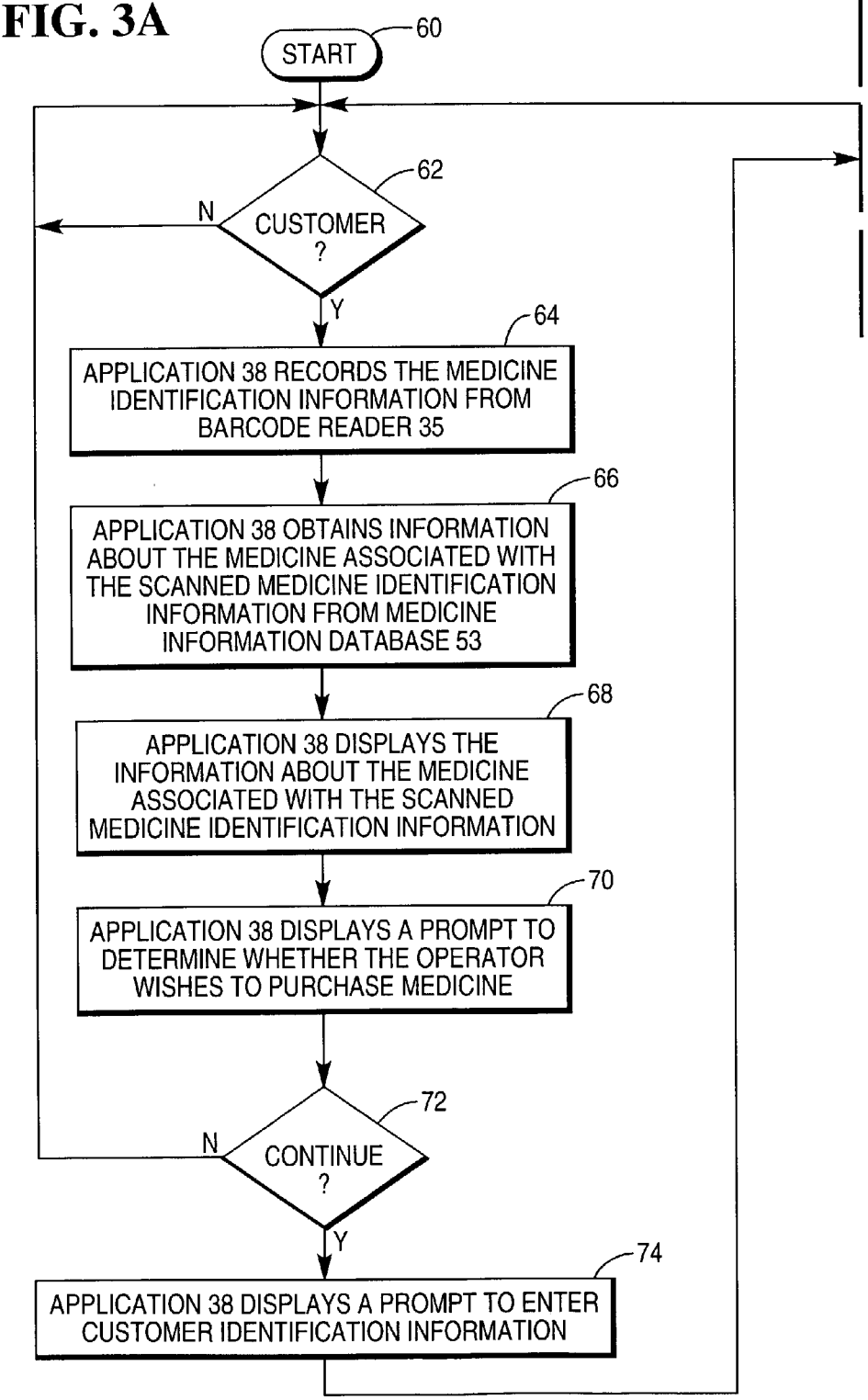

Turning now to FIG. 3, operation of application 38 is illustrated in detail beginning with START 60.

In step 62, application 38 waits for a pharmacy customer or operator. During this time, kiosk 12 may display advertisements or instructions, such as an instruction to scan a barcode on a medicine container or receipt from a previous transaction or other paper. An operator wishing to know drug interaction information approaches kiosk 12 and scans a barcode label on a medicine container or receipt.

In step 64, application 38 records the medicine identification information from barcode reader 35. Application 38 reads and decodes the barcode. Application 38 may use OPOS software to decode and then parse then decoded information from the OPOS software.

In step 66, application 38 obtains information about the medicine associated with the scanned medicine identification information from medicine information database 53.

In step 68, application 38 displays the information associated with the scanned medicine identification information. The information includes the name of the medicine and the prescription.

In step 70, application 38 displays a prompt to determine whether the operator wishes to purchase medicine.

In step 72, application 38 determines whether the operator wishes to continue. If the operator responds positively, operation continues to step 74. Otherwise, operation returns to step 62 to await another operator.

In step 74, application 38 displays a prompt to enter customer identification information.

In step 76, application 38 records the customer identification information. Application 38 may record customer information from touch screen 18 or card reader 24, if present.

In step 78, application 38 obtains all of the prescriptions under the customer identification information in customer database 52.

In step 80, application 38 obtains any interaction information between the scanned medicine and each of the prescription medicines from medicine information database 53.

In step 82, application 38 displays the interaction information.

In step 84, application 38 displays a prompt to the customer to determine whether the customer wishes to purchase the scanned medicine. If so, operation proceeds to step 82. Otherwise operation returns to step 62 to process other requests or wait for another customer.

In step 86, application 38 retrieves price information from prescription management software 50.

In step 88, application 38 processes payment for the order. In a first embodiment, application 38 processes payment directly. In a second embodiment, application 38 passes order details to self-service payment application 54 via interface 48. Application 38 receives notification of successful payment from self-service payment application 54. In either embodiment, application 38 may record customer signatures and store them electronically for later analysis.

In step 90, application 38 notifies prescription management software 50 that payment was successfully received. Prescription management software 50 updates the customer's account in customer database 52. A pharmacist may access customer database 52 through pharmacist terminal 56 to verify that payment has been received before filling the order. Operation returns to step 62 to wait for the next customer or the next request.

Although the present invention has been described with particular reference to certain preferred embodiments thereof, variations and modifications of the present invention can be effected within the spirit and scope of the following claims.

We claim:

1. A method for a pharmacy customer to determine interaction information between a medicine and other medicines utilizing a self-service pharmacy kiosk, the method comprising the steps of:
   (a) displaying a prompt to enter medicine identification information for the medicine on a display of the self-service pharmacy kiosk;
   (b) recording the medicine identification information provided by the pharmacy customer for the medicine;
   (c) using the medicine identification information to identify a particular type and dosage of medicine and to obtain details of the prescription of the medicine for the pharmacy customer for whom the medicine was prescribed, and obtaining interaction information for the prescribed medicine; and
   (d) displaying the interaction information to the pharmacy customer on the display of the self-service pharmacy kiosk.

2. The method as recited in claim 1, wherein step (a) further comprises displaying a prompt to scan a barcode for the medicine by a pharmacy kiosk and the method further comprises:
   scanning a barcode label containing the medicine identification information by the pharmacy customer utilizing a barcode reader which is part of the self-service pharmacy kiosk.

3. The method as recited in claim 1, further comprising:
   capturing a signature of the pharmacy customer utilizing a signature capture unit which is part of the self-service pharmacy kiosk; and
   storing the captured signature electronically.

4. The method as recited in claim 1 further comprising:
   executing an application by a processor in the self-service pharmacy kiosk to control the display to guide the pharmacy customer through a pharmacy transaction.

5. The method as recited in claim 1, wherein step (a) comprises the step of:
   (a-1) displaying a prompt to scan a barcode on a receipt for the medicine by a pharmacy kiosk.

6. The method as recited in claim 1, wherein step (c) comprises the step of:
   (c-1) communicating with a customer database to determine other medicines prescribed for the pharmacy customer and with an interaction database to obtain the interaction information by the self-service pharmacy kiosk.

7. The method as recited in claim 1, further comprising the steps of:
   (e) determining price information for the medicine by the self-service pharmacy kiosk; and
   (f) processing payment for the medicine by reading a pharmacy customer payment card with a card reader which is part of the self-service pharmacy kiosk.

8. A method for a pharmacy customer to determine interaction information between a medicine and other medicines using a self-service pharmacy kiosk, the method comprising the steps of:
   displaying a prompt to scan a barcode on a label containing medicine identification information for the medicine on a display of the self-service pharmacy kiosk;
   scanning the barcode utilizing a barcode reader which is part of the self-service pharmacy kiosk;
   obtaining the medicine identification information for the medicine by the pharmacy kiosk;
   using the medicine identification information to identify the medicine and particular type and dosage of the medicine and to obtain details of the prescription of the medicine for the pharmacy customer for whom the medicine was prescribed, and obtaining interaction information for the medicine by the self-service pharmacy kiosk communicating over a network connection with an interaction database; and
   displaying the interaction information on the display of the self-service pharmacy kiosk.

9. A method for a pharmacy customer to determine interaction information between a medicine and other medicines utilizing a self-service pharmacy kiosk, the method comprising the steps of:
   (a) displaying to the pharmacy customer a prompt to enter medicine identification information for the medicine on a display of the self-service pharmacy kiosk;
   (b) recording the medicine identification information for the medicine by the pharmacy kiosk;
   (c) displaying to the pharmacy customer a prompt to enter pharmacy customer identification information;
   (d) recording the pharmacy customer identification information provided by the pharmacy customer;
   (e) obtaining other prescriptions of the pharmacy customer for other medicines taken by the pharmacy customer using the pharmacy customer identification information;
   (f) using the medicine identification information and other prescriptions information to determine interaction information between the medicine, and the other medicines, by the self-service pharmacy kiosk; and
   (g) displaying the interaction information on the display of the self-service pharmacy kiosk.

10. The method as recited in claim 9, wherein step (a) further comprises:
(a-1) displaying on the display of the self-service pharmacy kiosk a prompt to scan a barcode for the medicine.

11. The method as recited in claim 9, wherein step (a) further comprises:
(a-1) displaying on the display of the self-service pharmacy kiosk a prompt to scan a barcode on a container for the medicine.

12. The method as recited in claim 9, wherein step (a) further comprises:
(a-1) displaying on the display of the self-service pharmacy kiosk a prompt to scan a barcode on a label for the medicine.

13. The method as recited in claim 9, wherein step (a) further comprises:
(a-1) displaying on the display of the self-service pharmacy kiosk a prompt to scan a barcode on a receipt for the medicine.

14. The method as recited in claim 9, wherein step (d) further comprises:
(d-1) recording the pharmacy customer identification information by reading a pharmacy customer's card with a card reader which is part of the self-service pharmacy kiosk.

15. The method as recited in claim 9, wherein step (d) further comprises:
(d-1) recording the pharmacy customer identification information utilizing a touch screen which is part of the self-service pharmacy kiosk.

16. The method as recited in claim 9, wherein step (f) further comprises:
(f-1) obtaining the interaction information from an interaction database by the self-service pharmacy kiosk.

17. The method as recited in claim 9, further comprising:
(h) determining price information for the medicine by the self-service pharmacy kiosk; and
(i) processing payment for the medicine by the self-service pharmacy kiosk.

18. A method for a pharmacy customer to determine interaction information between a medicine and other medicines utilizing a self-service pharmacy kiosk, the method comprising the steps of:
(a) displaying a prompt to scan a barcode on a label containing medicine identification information for the medicine on a display of the self-service pharmacy kiosk operated by the pharmacy customer;
(b) obtaining the medicine identification information for the medicine entered by the pharmacy customer utilizing a barcode reader which is part of the self-service pharmacy kiosk;
(c) displaying a prompt for the pharmacy customer to enter pharmacy customer identification information on the display of the self-service pharmacy kiosk;
(d) recording the pharmacy customer identification information entered by the pharmacy customer utilizing the self-service pharmacy kiosk;
(e) obtaining prescriptions for other medicines used by the pharmacy customer using the pharmacy customer identification information;
(f) using the medicine identification information to identify a particular type and dosage of medicine and to obtain details of the prescription of the medicine for the pharmacy customer, and obtaining interaction information between the medicine and the other medicines, from an interaction database by the self-service pharmacy kiosk communicating with the interaction database; and
(g) displaying the interaction information on the display of the self-service pharmacy kiosk.

* * * * *